US005524475A

United States Patent [19]
Kolpak et al.

[11] Patent Number: 5,524,475
[45] Date of Patent: Jun. 11, 1996

[54] MEASURING VIBRATION OF A FLUID STREAM TO DETERMINE GAS FRACTION

[75] Inventors: Miroslav M. Kolpak, Dallas, Tex.; Terry J. Rock, Farmington, N.M.

[73] Assignee: Atlantic Richfield Company, Los Angeles, Calif.

[21] Appl. No.: 336,900

[22] Filed: Nov. 10, 1994

[51] Int. Cl.⁶ .................................................. G01N 29/02
[52] U.S. Cl. ...................... 73/19.03; 73/61.45; 73/61.49; 73/61.79; 73/19.10; 73/64.53
[58] Field of Search ................... 73/19.01, 19.03, 73/19.1, 24.01, 61.41, 61.43–61.45, 61.49, 61.79, 64.53, 861.04

[56] References Cited

U.S. PATENT DOCUMENTS

| | | | |
|---|---|---|---|
| 3,283,562 | 11/1966 | Heisig et al. | 73/19.1 |
| 3,426,593 | 2/1969 | Jacobs | 73/64.53 |
| 4,080,837 | 3/1978 | Alexander et al. | 73/61.44 |
| 4,112,735 | 9/1978 | McKnight | 73/19.03 |
| 4,135,387 | 1/1979 | Benedict | 73/64.53 |
| 4,423,623 | 1/1984 | Ho et al. | 73/61.41 |
| 4,660,414 | 4/1987 | Hatton et al. | 73/61.44 |
| 4,696,191 | 9/1987 | Claytor et al. | 73/19.01 |
| 4,788,852 | 12/1988 | Martin et al. | 73/61.44 |
| 4,836,032 | 6/1989 | Redus et al. | 73/861.04 |
| 4,852,395 | 8/1989 | Kolpak | 73/61.1 R |
| 4,891,969 | 1/1990 | Wayland et al. | 73/61.44 |
| 5,083,452 | 1/1992 | Hope | 73/61.49 |
| 5,090,253 | 2/1992 | Kolpak | 73/861.38 |
| 5,150,061 | 9/1992 | Castel et al. | 73/61.41 |
| 5,259,250 | 11/1993 | Kolpak | 73/861.38 |
| 5,389,883 | 2/1995 | Harper | 73/61.44 |

FOREIGN PATENT DOCUMENTS

| | | | |
|---|---|---|---|
| 1110866 | 2/1956 | France | 73/24.01 |
| 4140572 | 6/1992 | Germany | 73/61.49 |
| 4019 | 1/1980 | Japan | 73/24.01 |
| 253864 | 12/1985 | Japan | 73/61.49 |
| 838552 | 6/1981 | U.S.S.R. | 73/19.03 |
| 1231453 | 3/1986 | U.S.S.R. | 73/61.79 |
| 1237965 | 6/1986 | U.S.S.R. | 73/24.01 |
| 1437772 | 11/1988 | U.S.S.R. | 73/19.03 |

Primary Examiner—Hezron E. Williams
Assistant Examiner—Daniel S. Larkin
Attorney, Agent, or Firm—Michael E. Martin

[57] ABSTRACT

Multiphase fluid flowstreams may be analyzed to determine to gas fraction of the fluid by defining a zone in a conduit in which the fluid flowstream is caused to vibrate either laterally or longitudinally at a resonant frequency of vibration of the fluid flowstream using a transducer or by causing the fluid to flow through an orifice in the conduit. A vibrating zone within the conduit is delimited by spaced apart ports in the conduit and/or spaced apart grilles which reflect the longitudinal vibrations. Lateral vibrations may be enhanced by causing the flowstream to flow through a rectangular passage in the conduit. Spectral analysis of the vibrating flowstream identifies the resonant frequency of vibration which, together with pressure and temperature measurements may be used in calculating the gas fraction.

5 Claims, 2 Drawing Sheets

MEASURING VIBRATION OF A FLUID STREAM TO DETERMINE GAS FRACTION

BACKGROUND OF THE INVENTION

1. Field of the Invention

The present invention pertains to a method for determining the gas fraction in a multiphase (liquid and gas) fluid stream by measuring induced vibrations of the fluid stream to determine a resonant vibration frequency.

2. Background

Various systems and methods have been developed to measure the volumetric and mass fraction of the components of a multiphase (gas and liquid) fluid flowstream. In the production of oil and gas, for example, it is particularly desirable to be able to measure the gas fraction of the production flowstream emanating from one or more wells without requiring separation of the gas from the liquid at the wellhead, for example. Various devices and systems have been developed for measuring the volumetric fraction of gas in the total flowstream, including systems which utilize gamma ray type densitometers, coriolis type flow meters, differential pressure measurement systems and dielectric constant measurement devices. Systems which utilize gamma ray type densitometers suffer from low sensitivity and the burdens of managing nuclear devices. Coriolis type meters have a pressure limit of about 1500 psig and a gas fraction limit in the flowstream of about 10% to 20%. Differential pressure measurement systems are relatively complicated and dielectric constant measurement devices sometimes suffer from poor accuracy at high gas fraction conditions in the flowstream and they are sensitive to changes in the components of the flowstream such as, wherein the liquid component is a mixture of oil and water.

Miroslav M. Kolpak U.S. Pat. Nos. 5,090,253 and 5,259,250 assigned to the assignee of the present invention disclose and claim multiphase fluid flow measurement systems wherein the density and gas fraction of the flowstream may be determined by vibrating a tube containing the flowstream over a range of frequencies and measuring the phase angle and amplitude of the fluctuating fluid pressures of the flowstream compared with the acceleration of the tube to determine the "sloshing" natural frequency of the fluid mixture. However, the power requirement for vibrating the tube or tubes may exceed that which would be available at remote measurement locations, such as wellheads located in Arctic oil fields of the North Slope of Alaska, for example. Accordingly, there continues to be a need to develop a multiphase fluid flow measurement system and method which is particularly attractive for measuring the gas fraction in the total fluid flowstream on a volumetric basis, in particular. It is to this end that the present invention has been developed.

SUMMARY OF THE INVENTION

The present invention pertains to a system and method for measuring the gas fraction in a multiphase (gas and liquid) fluid flowstream which includes measurement of the resonant frequency of vibration of the fluid flowstream.

In accordance with an important aspect of the invention, a multiphase fluid flowstream is caused to vibrate either laterally, that is perpendicular to the direction of flow of the flowstream, or longitudinally, that is in substantially the same direction as the direction of flow of the flowstream, and the resonant vibration frequency is determined and used to determine the volumetric fraction of the fluid flowstream which is composed of gas.

In accordance with another aspect of the invention a system is provided wherein lateral vibration of the fluid flowstream is induced and the resonant frequency of vibration in a lateral direction is measured to determine the gas fraction of the flowstream.

Still further, systems are provided which are operable to induce longitudinal vibrations of a fluid flowstream and measurements of the resonant frequency of vibration are carried out to determine the volumetric fraction of gas in the fluid flowstream. The systems include means for concentrating or limiting the portion of the fluid flowstream which is subject to vibration, which means may include spaced apart ports in a conduit which is conducting the flowstream therethrough and which define a measurement section of the system. Alternatively, the system may include spaced apart grille type reflectors for confining the axial vibrations over a predetermined length of conduit within which the vibrations are induced and measured.

The invention further contemplates the provision of a system for measuring the axial or longitudinal resonant frequency of vibration of a multiphase fluid flowstream wherein vibration is induced by an orifice and the axially or longitudinally resonating zone of a conduit conducting the flowstream is determined by the orifice and a port disposed downstream of the orifice. By measuring the resonant frequency of vibration of the multiphase fluid stream together with a prior determination of liquid density, gas density, and the measured pressure and temperature of the fluid flowstream together with a predetermined gas compressibility coefficient, a calibration coefficient and a predetermined adiabatic compression exponent for the gas, the gas fraction may be calculated using such parameters directly and result of measurement of the resonant frequency of vibration of the stream.

Those skilled in the art will further appreciate the above-noted advantages and unique features of the invention together with other superior aspects thereof upon reading the detailed description which follows in conjunction with the drawing.

DESCRIPTION OF PREFERRED EMBODIMENTS

Figure 1:
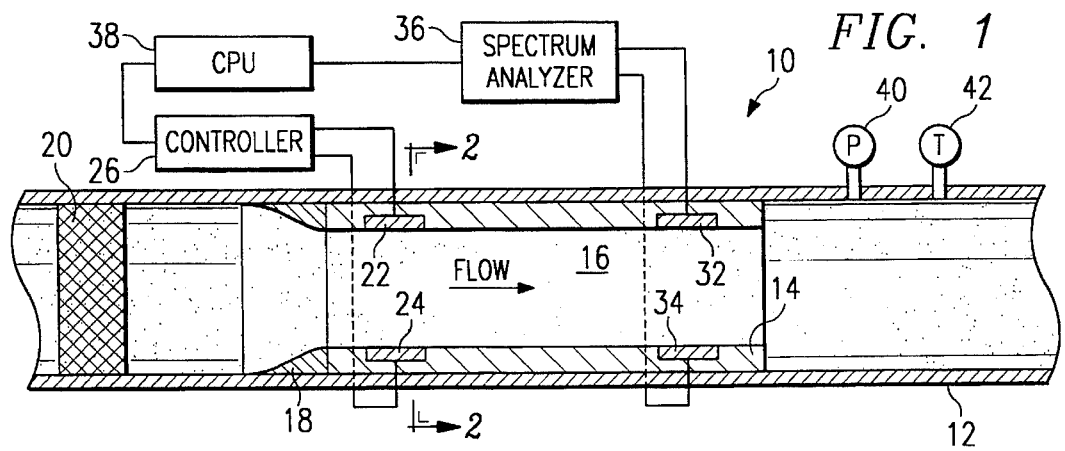
FIG. 1 is a schematic diagram of one preferred embodiment of a system for measuring the gas fraction of a multiphase fluid flowstream in accordance with the present invention.

In the description which follows like elements are marked throughout the specification and drawing with the same reference numerals, respectively. The drawing figures are not intended to be to scale and certain features are shown in schematic form in the interest of clarity and conciseness.

The present invention contemplates that the gas fraction of a multiphase fluid flowstream can be determined by causing the flowstream within a conduit to vibrate either laterally or longitudinally as it passes through a particular section of conduit and by measuring the resonant frequency of vibration of the flowstream within the measurement section. Since the resonant frequency of vibration of a mechanical system is dependent on the spring constant and the mass of the system. The spring constant for a volume of gas can be obtained if the pressure, temperature, specific gravity and compressibility factor are known. In many applications properties of a gas such as its specific gravity and compressibility factor within a range of pressures and temperatures can be easily predetermined. For example, in the production of oil and gas from subterranean earth formations it may be assumed that the gas is substantially methane or a sample of the gas flowstream may be taken from time to time and the gas properties such as specific gravity and compressibility factor easily predetermined. Moreover, in accordance with the invention the vibration of a multiphase fluid flowstream within a predetermined vibration zone in a conduit may be assumed to be an adiabatic process. Accordingly, the adiabatic compression exponent for the gas in question may also be easily predetermined. Still further, in combination liquid and gas flowstreams from wells or other sources, the liquid density may be easily predetermined and the gas density may be measured based on the pressure and temperature of the vibrating flowstream, the specific gravity of the gas and the compressibility coefficient.

The gas fraction of a fluid flowstream which is vibrated at a resonant frequency of the stream may be determined from the following equation:

$$f_g = \frac{1 \pm \sqrt{1 - 4(1 - \gamma_G/\gamma_L)\left(\frac{2n-1}{nc^2}\right)\left(\frac{g}{\gamma_L}\right)\left(\frac{P}{f_r^2}\right)}}{2(1 - \gamma_G/\gamma_L)}$$

stream; 1/sec., $\gamma_L$=liquid density; lbs/ft$^3$, $\gamma_G$=(29)(SG)(P)/10.73(z)(T) which is gas density in lbs/ft$^3$ P=measured pressure; psia, SG=gas specific gravity (air=1), T=measured temperature; 460+degF., z=gas compressibility coefficient, g=32.2 ft/sec$^2$, n=gas adiabatic compression exponent, and c=calibration coefficient.

The coefficient, c, is expressed in units of volume and is determined empirically, that is by calibration, for the particular conduit configuration which is used to make the resonant frequency measurements. Since the value of the coefficient, c, may not be precisely the same as the volume of the measurement section, an empirical calibration value should be derived for measurements of flowstreams having different gas densities and gas fractions to arrive at a particular average value of the coefficient for a particular conduit geometric configuration.

The other parameters used to determine the gas fraction, $f_g$, from the above equation may be determined as follows. The gas adiabatic compression exponent may be predetermined from measuring a sample of the gas or from knowing the composition of the gas. The gas compressibility coefficient may also be predetermined based on knowledge of the type of gas and the pressure and temperature conditions prevailing in the measurement system. The temperature, T, and the pressure, P, are measured values and the gas specific gravity is predetermined at the same time that the adiabatic compression exponent is predetermined. Liquid density is assumed based on a sample of the multiphase fluid flowstream and gas gravity is predetermined at the same time that the adiabatic compression exponent is predetermined. Liquid density is assumed based on a sample of the multiphase fluid flowstream and gas density is, of course, as indicated above calculated based on the gas specific gravity, the gas compressibility coefficient, the fluid temperature and the fluid pressure in the measurement system.

The invention contemplates determining the resonant frequency of vibration of the multiphase fluid flowstream by inducing vibrations in a predetermined conduit measurement section using a suitable transmitter or transducer element which will effect vibration of the fluid flowstream without significant or measurable vibration of the conduit itself. Suitable transducers for inducing vibration of the fluid flowstream may comprise pairs of opposed piezoelectric elements or suitable driven flexible diaphragm members vibrated in timed relationship to each other. A single transducer element may also be used to effect vibration of the fluid. The fluid vibration frequencies may be sensed by a suitable sensor, again either a piezoelectric element or other suitable "microphone" operably connected to spectral analysis equipment for sensing the vibration frequency which appears to have the strongest amplitude of vibration and the lowest rate of decay, thereby identifying it as a resonant frequency.

Figure 2:
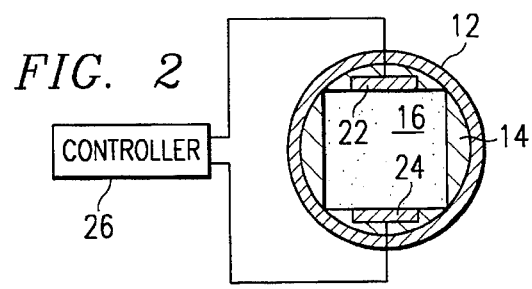
FIG. 2 is a sectional view taken generally along the line 2—2 of FIG. 1.

One preferred embodiment of a system for measuring the resonant frequency of vibration of a multiphase fluid flowstream is illustrated in FIGS. 1 and 2 and generally designated by the numeral 10. The system 10 includes a conventional cylindrical conduit 12 for conducting a multiphase fluid flowstream therethrough in the direction of the arrow marked "flow" in FIG. 1. The system 10 includes a section of the conduit 12 which is provided with a suitable liner 14 which changes the cross-sectional geometry of the conduit 12 from cylindrical to a generally rectangular or square passage 16. A suitable flow smoothing inducer 18 may be disposed upstream of the passage 16 as indicated in FIG. 1. Still further, it may be desirable to provide a flow mixing or homogenizing device 20 upstream of the measurement passage 16 and of a type commercially available.

Within the measurement section of the system 10 defined by the passage 16 is disposed a vibration inducing transducer arrangement comprising vibrating elements 22 and 24 which are disposed opposed to each other on opposite sides of the passage 16. The transducer elements 22 and 24 are suitably connected to a power supply and controller, generally indicated by the numeral 26. The controller 26 is operable to generate suitable vibration of the elements 22 and 24 to effect lateral vibration of the fluid flow through the passage 16, that is vibration in a direction generally normal to the arrow marked "flow" in FIG. 1. The configuration of the liner 14 is such as to effect reflection of the vibrating flowstream within the confines of the passage 16 to minimize loss of vibration activity to thereby provide for more suitable measurement of a resonant frequency of vibration. In this regard, the system 10 is provided with suitable sensors or microphones 32 and 34 which are disposed downstream from the transducer elements 22 and 24 as indicated. The sensors 32 and 34 may also be a piezoelectric type element or other suitable mechanical element which is operable to generate an electrical signal proportional to the amplitude and rate of deflection which occurs as a result of lateral vibration of the fluid flowing through the passage 16. Signals from the sensors 32 and 34 are transmitted to a suitable spectral analysis device or so called spectrum analyzer 36 which is capable of measuring the various frequencies of vibration of the fluid flowstream and identifying a resonant frequency of vibration. The resonant frequency of vibration signal may then be transmitted to a suitable digital computer or "CPU" 38 for performing a calculation of the gas fraction of the fluid flowstream in accordance with the method of the invention.

Accordingly, as a somewhat homogenized or thoroughly mixed multiphase fluid flowstream passes through the passage 16 it is caused to vibrate laterally, and possibly longitudinally, and to cause reflection of the vibration which may effect a general jumble of "noise" containing a broad band of vibration frequencies. Moreover, the vibration source comprising the transducer elements 22 and 24 may be operated to generate a broad band of frequencies which will cause echoes and, with time, the frequencies of vibration will decay as the energy input to the flowstream propagates away from the general area of the source of vibration. However, vibrations at the natural frequency of vibration ($f_r$) of the flowstream will decay at the slowest rate. In this way the spectrum analyzer 36 is operable to identify the resonant frequency of vibration of the flowstream in the passage 16. The system 10 also includes suitable pressure and temperature measuring devices 40 and 42 whose output signals may be directly communicated to the CPU 38 for calculating the gas fraction of the flowstream in accordance with the invention.

The elasticity and density differences between the gassy liquid flowstream and a material, such as steel, of which the conduit 12 and liner 14 are typically made should provide resonant frequencies of vibration of the conduit and the liner to be of much higher values than the resonant frequency of vibration of the flowstream. Accordingly, these vibrations should be readily identifiable and operable to be filtered out of the data being acquired for analysis by the spectrum analyzer 36 and the CPU 38.

The vibration source comprising the power supply and controller 26 and the transducer elements 22 and/or 24 may also be operated to repeatedly generate a range of frequencies of vibration to be input to the flowstream flowing through the passages 16. This inputting of a range of frequencies of vibration will cause echoes and a general development of "noise" in the flowstream and in the conduit 12 and liner 14. Again, however, vibrations at the natural frequency or resonant frequency of vibration of the fluid flowstream will register the highest level of energy at the sensors 32 and 34. Accordingly, the spectrum analyzer 36 can easily determine the value of the resonant frequency of vibration of the flowstream, $f_r$, by searching the sensor data for the frequency at which vibration power is the greatest.

Figure 3:
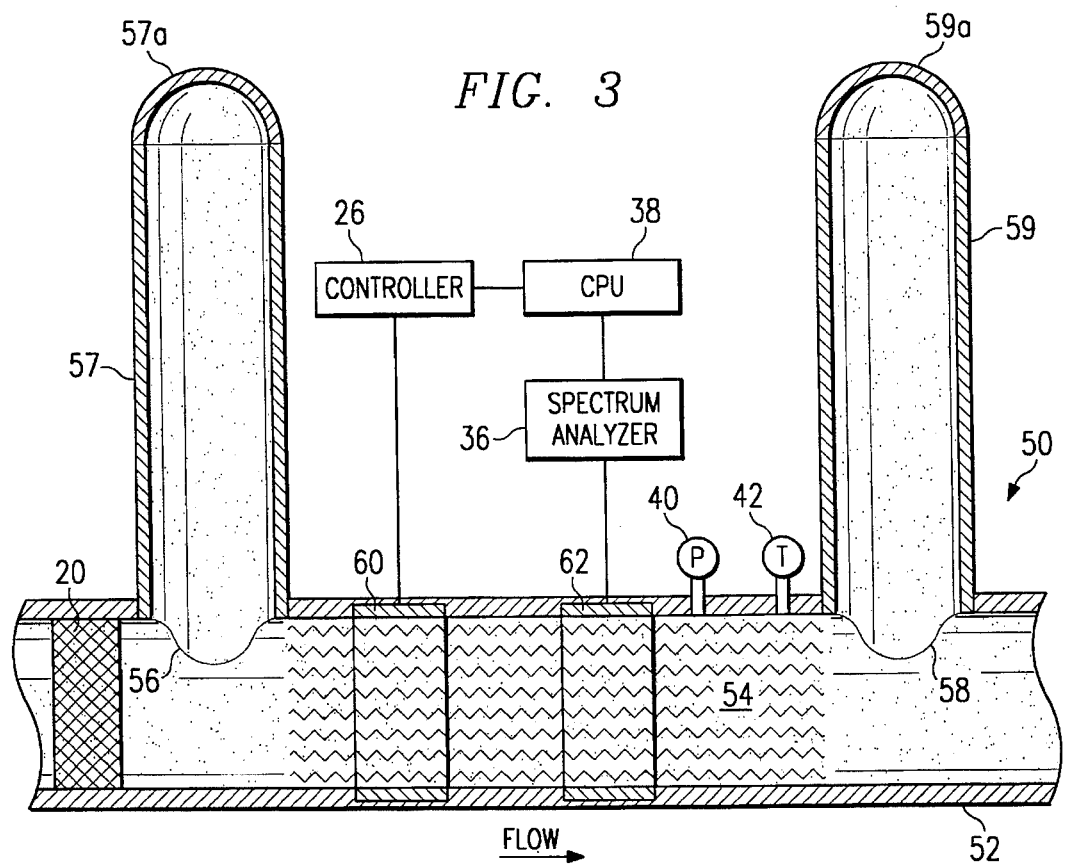
FIG. 3 is a schematic diagram of a first alternate embodiment of a system in accordance with the present invention.

Referring now to FIG. 3, there is illustrated another embodiment of a system in accordance with the invention for measuring the gas fraction of a multiphase fluid flowstream, which system is generally designated by the numeral 50. The system 50 includes a generally cylindrical conduit 52 having the flow mixer 20 interposed therein. The conduit 52 defines a zone 54 between spaced apart ports 56 and 58 in which longitudinally induced vibrations of the fluid flowstream may be effected by a transducer 60 suitably connected to the controller 26. A sensor 62 is spaced axially from the transducer 60 within the zone 54 and is operably connected to the spectrum analyzer 36 and the CPU 38 as indicated. The configuration of the transducer 60 may be one of a generally circumfrential or ring like element which is capable of deflecting in such a way as to induce axially or longitudinally propagating vibrations of the fluid flowstream in the zone 54 as it flows through the conduit 52. In like manner, the sensor 62 may be configured to sense or measure the frequency and amplitude of the vibrations propagated within the zone 54. The positions of the transducer 60 and the sensor 62 may be reversed, that is the transducer for generating the axially propagating vibrations may be disposed downstream of the sensor for measuring the vibrations. This alternate arrangement of transducer and sensor may be provided for each of the embodiments of the invention described herein.

Referring further to FIG. 3, the ports 56 and 58, which define the length of the zone 54, are each suitably closed by branch conduits 57 and 59, respectively, which have suitable closures or end caps 57a and 59a provided therefor. Thanks to the provision of the ports 56 and 58 the energy of vibration is confined to the zone 54 which will provide for more effective analysis or reading of the resonant vibration of the fluid flowing through the zone 54 by the spectrum analyzer 36.

Figure 4:
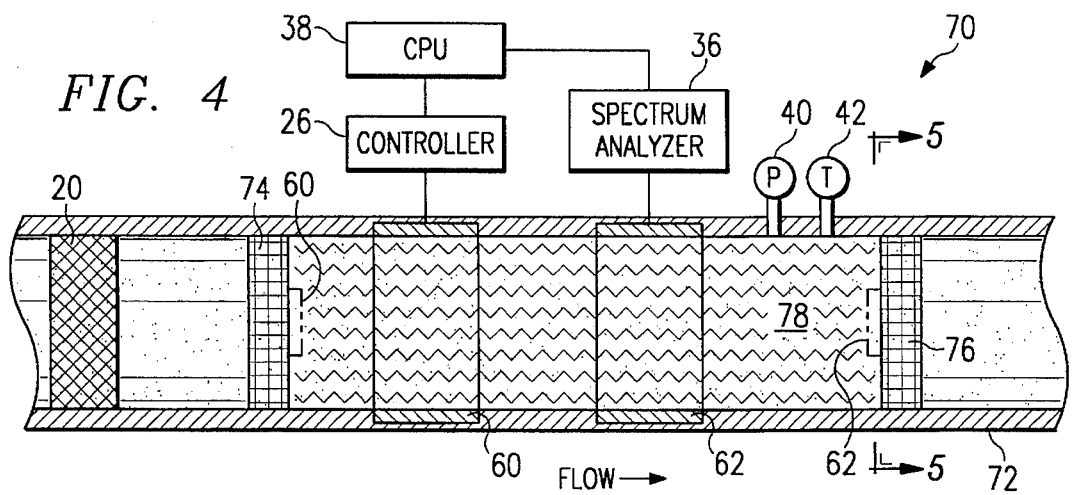
FIG. 4 is a schematic diagram of a second alternate embodiment of a system in accordance with the invention.

Referring now to FIG. 4, still another embodiment of a system for measuring the gas fraction of a fluid flowstream in accordance with the invention is illustrated and generally designated by the numeral 70. The system 70 includes a generally cylindrical conduit 72 for conducting a multiphase fluid flowstream therethrough in the direction of the arrow marked "flow". A suitable flow mixer 20 is interposed in the conduit 72 upstream of a pair of a spaced apart foraminous partitions or grilles 74 and 76. The grilles 74 and 76 serve as reflectors for delimiting a zone 78 in which axial vibrations may be induced by a transducer 60 operably coupled to a power supply and controller 26. A vibration sensor 62 is also interposed in the zone 78 between grilles 74 and 76 and is operably connected to the spectrum analyzer 36 as indicated.

Figure 5:
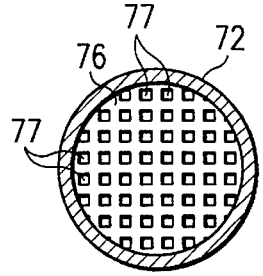
FIG. 5 is a section view taken along the line 5—5 of FIG. 4.

As shown in FIG. 5, the grilles 74 and 76 (grille 76 shown by way of example) are provided with a suitable number of perforations or openings 77 which are of a dimension less than a quarter wave length of the lowest expected resonant vibration of the fluid flowstream in the zone 78. In this way the grilles 74 and 76 tend to reflect most of the energy of vibration of the flowstream within the zone 78. As shown in FIG. 4, an alternate location for the transducer 60 and the sensor 62 would be to place these elements on the respective grilles 74 and 76 as indicated for possibly more effective generation of axial propagating vibrations and measurement of such vibrations, respectively. The configuration of the transducer 60 and the sensor 62, if placed on the grilles 74 and 76, would be such as to minimize the reduction in cross-sectional area of the conduit 72 so that fluid flow would not be significantly impeded.

Figure 6:
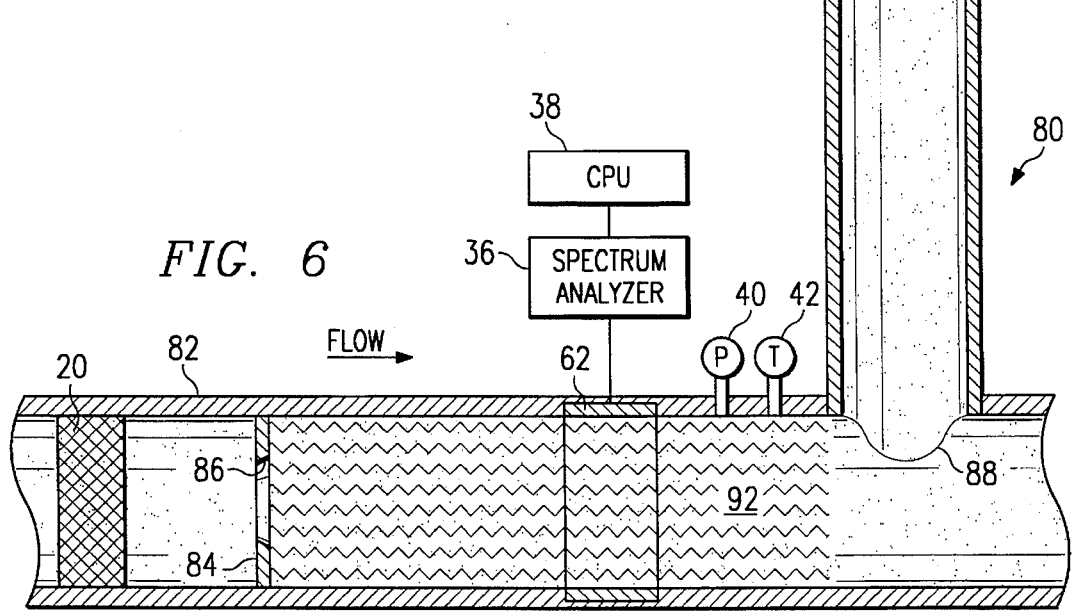
FIG. 6 is a schematic diagram of a third alternate embodiment of a system in accordance with the invention.

Referring now FIG. 6, yet another embodiment of a system for determining the gas fraction of a multiphase fluid flowstream is illustrated and generally designated by numeral 80. The system 80 may be advantageous for applications wherein minimum electrical energy is available for operating the system and performing the method and for minimizing modification of flow conduits in which the gas fraction measurement is desired to be obtained. The system 80 includes a generally cylindrical conduit 82, preferably having the flow mixing device 20 interposed therein upstream of an orifice plate 84 having a suitable sharp edge orifice 86 formed therein. Downstream of the orifice plate 84 is a port 88 formed in the wall of the conduit 82 and closed by a branch conduit 90 having a suitable closure 90a. The port 88 and the orifice plate 84 define a zone 92 therebetween within the conduit 82 in which the fluid flowstream may vibrate longitudinally or axially within the conduit. Vibrations are induced by the fluid flowing through the orifice 86 and are detected by a sensor 62 suitably connected to the spectrum analyzer 36 and the CPU 38.

Accordingly, in the system 80 vibrations are induced by the flow of the fluid itself through the orifice 86 without a specific device for inciting the vibrations. Moreover, a resonating cavity or zone 92 is defined by the position of the port 88 and the orifice plate 84 and the only add on device is the sensor 62 for sensing the frequency and amplitude of vibrations propagating within the zone 92. The system 80 is desirable for retrofitting existing orifice meter arrangements in fluid handling conduits. The systems 10, 50, 70, and 80 may also be modified to measure the mass flow of the multiphase fluid flowstream flowing therethrough by further modifying the systems to include a differential pressure measurement system and method in accordance with our copending U.S. patent application Ser. No. 08/255,139, filed Jun. 7, 1994.

The operation of systems 10, 50, 70 and 80 is believed to be understandable to those of skill in the art from the foregoing description of the systems. Each of the systems may be operated substantially continuously to monitor the gas fraction of a fluid flowstream. Each of the systems may also be operated in the mode wherein the transducer of the systems 10, 50, and 70, for example, is either operated to provide a short burst of energy to generate vibrations or the transducer is operated to input a range of frequencies of vibration to the fluid flowstream. In both instances the sensors 32, 34 and 62 and the spectrum analyzer 36 operate to provide a signal indicating the vibration frequency which has the longest decay time or the peak energy of vibration indicating that frequency to be the resonant frequency of vibration of the fluid flowstream. The computer or CPU 38 may be suitably programmed to make the calculation of the gas fraction based on the input data of measured temperature, pressure and the resonant frequency of vibration as well as the predetermined liquid density, gas specific gravity, gas compressibility coefficient, gas adiabatic compression exponent, the calibration coefficient of the volume of the zone in which vibrations are occurring and the calculated volume of gas density based on the measured values of pressure and temperature. The materials used for construction of the systems 10, 50, 70 and 90 may be conventional materials used for fluid conducting conduits and instruments and the transducer 60 and the sensor 62, as well as the transducers 22 and 24 and the sensors 32 and 34 may be provided from types of devices which are known to those of skill in the art.

Although preferred embodiments of the invention have been described in detail herein, those skilled in the art will also recognize that certain substitutions and modifications may be made without departing from the scope and spirit of the invention as recited in the appended claims.

What is claimed is:

1. A system for determining the gas fraction of a multiphase, gas and liquid, fluid flowstream comprising:

conduit means for conducting said fluid flowstream therethrough;

means defining a zone within said conduit means;

means within said zone for vibrating said fluid flowstream at a resonant frequency thereof;

a sensor within said zone and spaced from said means for vibrating for sensing the frequency and amplitude of vibration of said fluid flowstream in said zone; and a spectrum analyzer for identifying a resonant frequency of vibration of said fluid flowstream.

2. The system set forth in claim 1 including:

a fluid flow mixing device interposed in said conduit upstream of said zone with respect to the direction of flow of fluid through said conduit means.

3. The system set forth in claim 1 wherein:

said means for inducing vibrations of said fluid flowstream comprises a transducer disposed to effect vibration of said fluid flowstream in said conduit means in a direction substantially normal to the direction of flow of said fluid flowstream.

4. The system set forth in claim 3 wherein said means for defining said zone includes:

a liner in said conduit having a substantially rectangular cross-section passage therethrough and wherein said transducer is operable to induce vibrations of said fluid flowstream within said passage.

5. A method for determining the gas fraction of a multiphase, gas and liquid, fluid flowstream flowing through a zone of a fluid conducting conduit comprising the steps of:

measuring the pressure and temperature of said fluid flowstream in said zone;

determining the density of the gas in said zone based on the measured pressure and temperature;

inducing vibrations of said fluid flowstream in said zone by transducer means interposed in said conduit for effecting vibration of said fluid flowstream in at least one of a longitudinal direction and a lateral direction with respect to a direction of flow of said fluid flowstream;

causing said transducer means to vibrate in a predetermined range of frequencies of vibration to effect vibration of said fluid flowstream at a resonant frequency of said fluid flowstream;

measuring the resonant frequency of vibration of the fluid flowstream in said zone; and determining the gas fraction of said fluid flowstream based on the determined values of pressure, temperature, gas density and resonant frequency of vibration.

\* \* \* \* \*